United States Patent [19]

Genshaw

[11] 4,057,394
[45] Nov. 8, 1977

[54] TEST DEVICE AND METHOD FOR DETERMINING BLOOD HEMOGLOBIN

[75] Inventor: Marvin Alden Genshaw, Elkhart, Ind.

[73] Assignee: Miles Laboratories, Inc., Elkhart, Ind.

[21] Appl. No.: 688,981

[22] Filed: May 24, 1976

[51] Int. Cl.$^2$ .................. G01N 31/22; G01N 33/16
[52] U.S. Cl. .................... 23/230 B; 23/253 TP; 356/40
[58] Field of Search ........... 23/230 B, 253 TP, 253 R, 23/232 R, 254 R; 356/40; 116/114 AM

[56] References Cited

U.S. PATENT DOCUMENTS

| | | | |
|---|---|---|---|
| 703,319 | 6/1902 | Tallqvist | 23/230 B |
| 2,118,144 | 5/1938 | Berman et al. | 116/114 AM |
| 2,567,251 | 9/1951 | Stitt | 23/232 R |
| 2,569,895 | 10/1951 | Main-Smith et al. | 23/254 R |
| 2,799,167 | 7/1957 | Loconti | 23/253 TP |
| 3,002,385 | 11/1961 | Wahl et al. | 23/253 TP |
| 3,033,655 | 5/1962 | Grosskopf | 23/254 R |
| 3,232,710 | 2/1966 | Rieckmann et al. | 23/253 TP |
| 3,311,084 | 3/1967 | Edenbaum | 23/253 TP |
| 3,350,175 | 10/1967 | McConnaughey et al. | 23/254 R |
| 3,420,635 | 1/1969 | Davis | 23/253 TP |
| 3,672,845 | 6/1972 | Verbeck | 23/253 TP |
| 3,723,064 | 3/1972 | Liotta | 23/253 TP X |
| 3,820,953 | 6/1974 | McEwan et al. | 116/114 AM X |

Primary Examiner—Robert M. Reese
Attorney, Agent, or Firm—Joseph C. Schwalbach; Roger Norman Coe

[57] ABSTRACT

A test device and method are provided for determining the hemoglobin content of blood. The test device comprises a substantially opaque light reflecting matrix having a refractive index significantly different from the refractive index of blood. In use, a test sample of blood is contacted with the matrix of said test device and the light reflectance therefrom is measured as an indication of the quantitative amount of hemoglobin present in said sample.

6 Claims, No Drawings

TEST DEVICE AND METHOD FOR DETERMINING BLOOD HEMOGLOBIN

BACKGROUND AND PRIOR ART

The determination of the hemoglobin content of blood has long been recognized as an invaluable aid to the medical practitioner in the diagnosis of many abnormal conditions. For instance, the condition of iron deficiency anemia in mammals, especially in humans, is well known. This condition, which may be caused by chemical poisoning, infection or disease, is generally characterized by a reduction in the amount of hemoglobin in the blood. Normally, the hemoglobin content in the blood of adult males varies between 12 and 16 grams (g) per 100 milliliters (ml) of blood and in adult females varies between 11 and 15 g per 100 ml of blood. Blood which contains much less than 12 g of hemoglobin per 100 ml of blood is then considered indicative of an anemic condition. In view of the importance of diagnosing such condition, it is considered highly desirable to provide a sensitive, rapid and reliable test for blood hemoglobin.

Various methods and devices are described in the literature for determining the hemoglobin content of blood. Usually, hemoglobin is measured as oxyhemoglobin or is first converted into one of several derivatives, such as alkaline hematin, acid hematin, cyanmethemoglobin or carboxyhemoglobin. The concentration of hemoglobin is then determined by comparing the color or absorbance of the unknown sample with a standard color reference. The method of comparison may be performed by visual matching of colors or by instruments which measure light absorbance of the sample at defined wavelengths. Unfortunately, these methods are often time consuming and require bulky equipment which must be consistently cleaned and maintained to produce reliable results.

Still another procedure is described by T. W. Tallqvist in Z. Klin. Med. 40, 137 (1900) and Arch. Gen. Med. 3, 421 (1900). In this method, a sample of undiluted blood is applied to an absorbent paper and the color of the blood saturated paper is then visually compared with a series of lithographed color standards to estimate the hemoglobin content. Although this procedure is reported to have a margin of error of between 20 and 50%, as discussed by M. M. Wintrobe, *Clinical Hematology,* Lea and Febiger, Philadelphia, 1961, Page 393, it is still followed by some physicians because of its simplicity. Attempts to quantify the Tallqvist procedure instrumentally by applying light absorption techniques or more recently light reflectance measurements have not been successful due to relatively large margins of error encountered in light absorbance or reflectance measurements.

Several commercially available analytical devices specifically intended for the detection of blood constituents or of bacteria have been tried unsuccessfully by those skilled in the art to estimate hemoglobin content of blood. For example, multilayer devices described in U.S. Pat. Nos. 3,552,925; 3,552,928; or German Offenlegunschrift No. 2,332,760 provide various means, such as porous membranes or filtering layers, for separating red blood corpuscles from blood samples prior to the detection of constituents in the serum; and bacterial detection devices described in U.S. Pat. No. 3,764,480, provide means for detecting surface bacteria by reflectance measurements. It was thought that the hemoglobin content of blood could be estimated be use of these devices and instrumental means. The attempts, however, to quantify these various analytical devices for the detection of hemoglobin content by applying light reflectance or absorption techniques have not been successful due to relatively large margins of error encountered in light reflectance or absorbance measurements.

SUMMARY OF THE INVENTION

In accordance with the present invention, a test device and method are provided for determining the hemoglobin content of blood which avoids the disadvantages of the prior art devices and methods discussed above. The test device comprises a substantially opaque light reflecting matrix having a refractive index significantly different from the refractive index of blood. The test device may also incorporate a carrier member to which said matrix is attached and air venting means for the matrix member. In use, a test sample of blood is contacted with the matrix of said test device and the light reflectance therefrom is measured as an indicator of the quantitative amount of hemoglobin present in said sample.

DESCRIPTION OF THE INVENTION

While it is known that the light reflectivity of a surface, i.e., the ratio of the light emission reflected from a surface to the whole incident light emission thereon, is related to the physical property and the light absorptive and scattering properties of the surface media and to the refractive indices of the media through which the light must pass, it will be appreciated by those skilled in the art that reflectivity is a complex phenomenon which is further complicated by the addition of a light absorbing substance, such as blood containing highly colored hemoglobin. It was indeed surprising, to the present inventor, to discover that the use of a matrix having an index of refraction significantly different from a blood sample not only increases the sensitivity of light reflectance measurements of the surfaces in contact with the blood sample, but also remarkedly improves the precision of such measurements and thereby overcomes the large margins of error encountered by prior art devices used for the determination of blood hemoglobin content by instrumental methods. The use of a matrix having an index of refraction close to or equal to that of a blood sample does not substantially improve the precision of light reflectance measurements.

Matrices which can be employed include those which are substantially opaque, light reflective, blood absorbent and have a refractive index significantly different from that of the blood sample, i.e., the refractive index of blood varies between about 1.3 and 1.4. Matrix refractive indices below about 1.0 or above about 1.7 to 1.8 are significantly different from the refractive index of blood to provide improved precision of light reflectance measurements. Such matrices may contain such materials as the white or light colored metals, metallic carbonates, oxides and sulfides which are insoluble in and unreactive with water or blood.

In one preferred mode of the present invention, the matrix is prepared by incorporating an opaque, light reflecting substance on or within a blood absorbent member by various well-known methods which include impregnating an absorbent material with a solvent mixture, suspension or emulsion of the light reflecting substance. Thereafter, the impregnated matrix is dried, thus incorporating on or within the matrix a finely divided, intimate, uniform mixture of the light reflecting substance. The dried impregnated matrix thusly prepared then may be advantageously affixed by suitable means to an acceptable carrier member for ease of use.

Suitable blood absorbent members which may be used are those which permit rapid and uniform penetration of the blood sample to be analyzed when applied to the surface of the matrix. Such materials include paper, cellulose, wood, synthetic resin fleeces, non-woven or woven fabrics and the like.

Suitable, light reflecting substances which may be used in this invention are substantially opaque and have an index of refraction significantly different from blood. Such materials include the white or light colored powdered metals, metallic carbonates, oxides and sulfides which are insoluble in and unreactive with water or blood serum. Specific examples of such materials and their mean refractive indices, at sodium D-line (589 nm) unless otherwise stated, are aluminum metal powder (0.78 at 434 nm), silver metal powder (0.18), lead carbonate (1.99), lead oxide (2.61), titanium dioxide (2.64), zinc oxide (2.02), zinc sulfide (2.37), zirconium oxide (2.17) and the like. Preferably, the light reflecting substance is incorporated on or within the absorbent member at a concentration which provides a light reflectance of between 30 and 70% of the incident light when the impregnated matrix is saturated with a blood sample, as the optimum precision in reflectance measurement occurs in this range.

In addition to the above light reflecting substance which actively participates in the measurement of hemoglobin content, further components, such as water soluble binders and wetting agents, may also be optionally included in the test device of the present invention. Thus, it may be useful in some instances to incorporate a thickening agent to bind the light reflecting substance to the absorbent member. Such water soluble binders or thickening agents include albumin, algin, carrageenin, casein, carboxy methyl cellulose, hydroxy ethyl cellulose, methyl cellulose, polyvinyl-pyrrolidone and the like. Surfactants, such as detergents, may also be added to improve the wetting properties of the matrix and promote hemolysis of the erythrocytes of blood, thus improving the homogeneity of the sample throughout the matrix and improving the precision of light reflectivity measurement. Such wetting agents include anionic, cationic or amphoteric detergents. Preferably, anionic detergents, such as sodium lauryl sulfate or any long chained organic sulfate or sulfonate, such as dioctyl sodium sulfosuccinate or sodium dodecyl benzene sulphonate and the like, may be used.

In use, a measured quantity of a blood sample is applied to the matrix of the test device of this invention and allowed to thoroughly permeate and saturate a portion of the matrix. Although the measured quantity applied to a specific matrix should be held constant to within about ±10 volume percent, the actual quantity of blood applied to the matrix may be widely varied depending upon the size and absorptive capacity of the particular matrix. It is essential, however, not to add an amount of blood in excess of the amount required to saturate the matrix. An excess amount of blood will cause the blood to form a thin film or pool at the surface and cause substantial change in the light reflectivity from the surface. The light reflected from the blood saturated surface is then measured using any reflectance meter capable of measuring diffuse reflectance at a fixed wavelength between about 300 and 620 nanometers (nm) with a sufficient resolution, precision, and stability to allow reflectance measurements to be made which will provide a determination to within about ±0.5 g of hemoglobin per 100 ml. The intensity of the light reflectance from the blood saturated matrix is inversely proportional to the amount of hemoglobin present in the blood sample. The actual amount of hemoglobin present in the blood is determined by reference to a standard curve prepared using known hemoglobin liquid standards or standard reflectance reference chips as is well known in the art. Although the time for making the reflectance reading is not critical, the reading should be made before evaporation of moisture causes changes in hemoglobin concentration. Usually the reflectance reading may be made over the time period of about 0.5 to 3 minutes after the blood is applied to the test device.

As described above, the matrix of this invention may be affixed to a holding means or carrier member for ease of use. A wide variety of materials may be selected for this purpose as long as the carrier member is not attached to the matrix member in such a fashion as to interfere with the rapid permeation and saturation of the blood sample into the matrix. As blood is a relatively viscous liquid, it is preferred with some matrices, such as some papers, to provide air venting means to allow the escape of air from the absorbent matrix upon the addition of the blood sample thereto. This is preferably accomplished by interposing an air venting layer between the matrix member and the carrier member.

The following illustrative examples are provided to further describe the invention but are not intended to limit the scope of the invention.

EXAMPLE I

This example illustrates a typical preparation of the test device of this invention and the method of using the same.

The following components were mixed to provide an impregnating emulsion.

| Component | Quantity |
| --- | --- |
| Water, deionized | 2000 cc |
| Benzene | 2000 cc |
| Titanium dioxide | 400 g |
| Sodium lauryl sulfate | 2.0 g |
| Methyl ethyl cellulose | 2.0 g |

The emulsion was prepared by mixing about 1000 cubic centimeters (cc) of water with the titanium dioxide in an ultrasonic agitator to aid in the dispersion of the titanium dioxide. The methyl ethyl cellulose was dissolved in about 200 cc of water on a heated magnetic stirrer and then added to the titanium dioxide suspension. The sodium lauryl sulfate was dissolved in 800 cc of water and added to the titanium dioxide suspension. The benzene was then added to the above suspension and the suspension was agitated to form the emulsion.

Whatman 3MM filter paper sheet matrices were impregnated with the above emulsion and dried. The thus impregnated paper matrices were then cut into convenient 1.016 cm by 30.48 centimeters (cm) (0.4 in by 12 in) strips. In addition, strips of 0.005 cm (0.002 in) polyester plastic sheet material, such as polystyrene terephthalate, 0.76 cm by 30.48 cm (0.3 in by 12 in), to be used as an air venting layer; strips of double-faced adhesive tape, 1.016 cm by 30.48 cm (0.4 in by 12 in); and strips of a flexible plastic sheet material, such as polystyrene, 0.018 cm by 9.53 cm by 30.48 cm (0.007 in by 3.75 in by 12 in) to be used as a carrier support member, were also prepared. A strip of the double-faced adhesive tape was then adhered to one face of a strip of the polystyrene sheet material parallel with and spaced 0.25 cm (0.1 in) from one longitudinal edge of the latter. A strip of the polyester plastic sheet material was then adhered to the exposed surface of the thus applied double-faced adhesive tape in centered longitudinal alignment therewith, leaving longitudinal edge portions of the tape about 0.13 cm (0.05 in) in width exposed along each side of the polyester plastic sheet material. An impregnated paper matrix strip was then placed on the polyester strip in registration adhesively with the double-faced tape, and the opposite longitudinal edge portions of the matrix strip were then adhesively affixed to the exposed longitudinal edge portions of the double-faced adhesive tape. The resulting 9.53 cm by 30.48 cm (3.75 in by 12 in) laminate was then cut transversely at 0.51 cm (0.2 in) intervals to provide finished test devices each measuring about 9.53 cm by 0.51 cm (3.75 in by 0.2 in).

A standard curve for use with these test devices was prepared using blood samples of known hemoglobin content, containing between 6.2 g and 18.5 g of hemoglobin per 100 ml of blood, to respectively saturate the absorbent paper matrix of a plurality of said devices. About 18 microliter ($\mu$l) of blood sample was applied to the major exposed surface of the respective impregnated paper matrices and allowed to thoroughly saturate the same. Usually the blood saturated the matrix within about 15 seconds. Light reflectance from the major exposed surface of each blood saturated matrix was then measured at 620 nm using a light reflectance instrument. The light reflectance measurements were found to vary linearly with variations in the hemoglobin content of the blood samples tested.

A total of 331 samples of blood were analyzed using the above test device and method. Hemoglobin contents were determined from the standard curve and the results were compared with the hemoglobin values of the same samples obtained using the standard cyanmethemoglobin assay method. The results of using the method and test device of this invention were found to vary from the value of the standard assay by a standard deviation of 0.7 g of hemoglobin per 100 ml of blood. This corresponds to a coefficient of variation of about 6%. Thus, the present method and device were found to be clinically useful for the determination of the hemoglobin concentration in whole blood.

EXAMPLE 2

This example illustrates the prior art Tallqvist method and device using a quantitative measurement of reflectance.

From sixty blood samples of known hemoglobin content, containing between 7.4 g and 19.4 g of hemoglobin per 100 ml of blood about 20 $\mu$l of each was used respectively to saturate 0.51 cm by 1.02 cm (0.2 in by 0.4 in) Whatman 3 MM paper matrices. Light reflectance from the surface of the blood saturated matrices was measured at 620 nm with a rapid scanning reflectance spectrophotometer. A linear regression analysis of the data gave a correlation coefficient of 0.68 with a residual standard deviation of 1.8 g percent hemoglobin. This corresponds to a coefficient of variation of 15%. Thus the Tallqvist method, even though using an instrumental determination of reflectance, did not provide a clinically useful means for determination of the hemoglobin concentration in whole blood.

EXAMPLE 3

This example illustrates an attempt to use the multilayer analytical device described in German Offenlegunschrift No. 2,332,760 for the detection of hemoglobin in whole blood. This device is specifically useful for detecting various constituents, such as glucose, uric acid, chloride ions, albumin and the like in bodily fluids, principally in blood. The multilayer devices include a translucent substrate, at least one reagent layer arranged on one side of the translucent substrate, a reflection layer arranged on the upper side of the reagent layer, and a filter or spreading layer arranged on the upper side of the reflection layer. In use, a test sample is applied to the upper exposed surface of the filter layer, for example, to filter out the red corpuscles of blood and to permit the serum to proceed to the layers underneath. When the serum containing the constituents to be detected permeates the reagent layer, a reaction occurs between the reagents contained therein and the sample constituents, usually to produce a color. The presence of the constituent is determined by spectrophotometric reflectance measurements which are taken through the translucent substrate.

In the preparation of this multilayer device, the following solutions were prepared:

| Solution 1: | Glucose Oxidase (2650 IU/cc) | 5 cc |
|---|---|---|
| | Calf skin gelatin (purified) | 9 g |
| | Peroxidase | 0.184 g |
| | o-dianisidine | 0.205 g |
| | H$_2$O | 90 cc |
| Solution 2: | Cellulose acetate | 1.5 g |
| | Titanium dioxide | 12 g |
| | Acetone | 90 cc |
| | Xylene | 40 cc |
| Solution 3: | Diatomaceous silica | 16.5 g |
| | Salicylic acid | 0.165 g |
| | Cellulose acetate | 1.65 g |
| | Dichloroethane | 60 cc |
| | Acetone | 50 cc |

Solution 1 was used to apply a film of 0.025 cm (0.010 in) thickness on a film substrate of 0.01 cm (0.004 in) thickness. This first layer was dried in air before subsequent films were applied. Solution 2 was used to apply a 0.025 cm (0.01 in) film over the first layer and dried to form a second layer. Solution 3 was used to apply a 0.025 cm (0.010 in) film over the first and second layers and dried to form a third layer. The thus-prepared multilayer device was then cut into 0.51 cm by 1.02 cm (0.2 by 0.4 in) pieces.

From blood samples of known hemoglobin content, containing between 8.9 g and 15.9 g of hemoglobin per 100 ml of blood, about 10 $\mu$l of each was used respectively to saturate the multilayer pieces by application of the blood to the upper surface thereof. Light reflectance from the upper surface of the blood saturated multilayer pieces was measured at 620 nm with a rapid scanning reflectance spectrophotometer. A linear regression analysis of the data gave a correlation coefficient of 0.67 with a residual standard deviation of 2.0 g percent hemoglobin. This corresponds to a coefficient of variation of 16.6%. Thus, this prior art multilayer device did not provide a clinically useful determination of the hemoglobin concentration in whole blood.

What is claimed is:

1. A method for determining the hemoglobin content of blood, which comprises contacting a test device with a sample of blood and measuring light at a wavelength of between about 300 and about 620 nanometers which is reflected from said test device, wherein said test device comprises a substantially opaque, light reflective, blood absorbent matrix having a refractive index of less than about 1.0 or above about 1.7.

2. The method of claim 1 in which the light reflected from said test device is measured within about 0.5 to about 3 minutes after the blood sample contacts said test device.

3. A test device for determining the hemaglobin content of a blood sample to an accuracy of about ± 0.5 grams of hemaglobin per 100 milliliters of the blood sample by a reflected light measurement made at a wavelength between about 300 and about 620 nanometers within about 0.5 and about 3 minutes after the blood sample is applied to said test device, which test device comprises a substantially opaque, light reflective, blood absorbent matrix having a refractive index of less than about 1.0 or above about 1.7 which is prepared by incorporating a blood absorbent member with a substantially opaque light reflecting substance selected from the class of white or light colored materials consisting of powdered metals, metallic carbonates, metallic oxide and metallic sulfides which are insoluble in and unreactive in said blood sample at a concentration providing a light reflectance of between about 30 and 70 percent of the incident light when the matrix is saturated with said blood sample, said test device including means for venting air from said blood absorbent matrix.

4. The test device according to claim 3 wherein said air venting means comprises an air venting layer interposed in laminate relation between the blood absorbent matrix and a carrier member.

5. A test device according to claim 3 wherein the opaque light reflecting substance is titanium dioxide.

6. A test device according to claim 3 wherein the blood absorbent member is also incorporated with a water soluble binder and a wetting agent.

* * * * *